US012646605B2

(12) United States Patent
Nikolskiy et al.

(10) Patent No.: US 12,646,605 B2
(45) Date of Patent: Jun. 2, 2026

(54) VIRTUAL DENTAL RESTORATION INSERTION VERIFICATION

(71) Applicant: James R. Glidewell Dental Ceramics, Inc., Newport Beach, CA (US)

(72) Inventors: Sergey Nikolskiy, Coto de Caza, CA (US); Fedor Chelnokov, Khimki (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 18/069,740

(22) Filed: Dec. 21, 2022

(65) Prior Publication Data

US 2023/0127620 A1        Apr. 27, 2023

Related U.S. Application Data

(63) Continuation of application No. 16/834,137, filed on Mar. 30, 2020, now Pat. No. 11,538,573.

(51) Int. Cl.
| | |
|---|---|
| *G16H 30/20* | (2018.01) |
| *A61C 13/00* | (2006.01) |
| *G06F 30/20* | (2020.01) |

(52) U.S. Cl.
CPC ......... *G16H 30/20* (2018.01); *A61C 13/0004* (2013.01); *G06F 30/20* (2020.01); *G05B 2219/45167* (2013.01); *G06T 2207/30036* (2013.01)

(58) Field of Classification Search
CPC ............... A61C 13/0004; G06F 30/20; G05B 2219/45167; G06T 2207/30036; G16H 30/20

USPC .......................................................... 705/2
See application file for complete search history.

(56) References Cited

U.S. PATENT DOCUMENTS

| | | | |
|---|---|---|---|
| 6,957,118 | B2 | 10/2005 | Kopelman et al. |
| 7,228,191 | B2 | 6/2007 | Hofmeister et al. |
| 7,236,842 | B2 | 6/2007 | Kopelman et al. |
| 7,333,874 | B2 | 2/2008 | Taub et al. |
| 7,689,310 | B2 | 3/2010 | Kopelman et al. |
| 7,735,542 | B2 | 6/2010 | Marshall et al. |
| 7,738,989 | B2 | 6/2010 | Taub et al. |
| 8,145,340 | B2 | 3/2012 | Taub et al. |
| 8,359,114 | B2 | 1/2013 | Steingart et al. |
| 8,457,772 | B2 | 6/2013 | Giasson et al. |
| 8,577,493 | B2 | 11/2013 | Taub et al. |
| 8,628,327 | B1 | 1/2014 | Blaisdell et al. |
| 8,909,363 | B2 | 12/2014 | Kopelman et al. |

(Continued)

FOREIGN PATENT DOCUMENTS

| | | |
|---|---|---|
| CA | 2580374 C | 3/2006 |
| EP | 2269539 A1 | 1/2011 |

(Continued)

OTHER PUBLICATIONS

Gino Van Den Bergen, Efficient Collision Detection of Complex Deformable Models using AABB Trees, Department of Mathematics and Computing Science, Eindhoven University of Technology, Nov. 6, 1998, in 14 pages.

(Continued)

*Primary Examiner* — Tuan C Dao

(74) *Attorney, Agent, or Firm* — Klarquist Sparkman, LLP

(57) ABSTRACT

A system and method include digitally determining a virtual insertion path of a digital dental restoration.

19 Claims, 14 Drawing Sheets

(56) References Cited

U.S. PATENT DOCUMENTS

| | | | |
|---|---|---|---|
| 9,308,055 B2 | 4/2016 | Fisker et al. | |
| 9,539,071 B2 | 1/2017 | Taub et al. | |
| 9,683,835 B2 | 6/2017 | Kopelman et al. | |
| 9,730,779 B2 | 8/2017 | Kopelman et al. | |
| 9,895,209 B2 | 2/2018 | Blaisdell et al. | |
| 10,016,260 B2 | 7/2018 | Blaisdell et al. | |
| 10,059,059 B2 | 8/2018 | Kopelman et al. | |
| 10,076,389 B2 | 9/2018 | Wu et al. | |
| 10,251,726 B2 | 4/2019 | Fisker et al. | |
| 10,327,878 B2 | 6/2019 | Kopelman et al. | |
| 10,406,753 B2 | 9/2019 | Kopelman et al. | |
| 10,568,720 B2 | 2/2020 | Liston et al. | |
| 11,351,015 B2 | 6/2022 | Leeson et al. | |
| 11,538,573 B2 | 12/2022 | Nikolskiy et al. | |
| 2002/0042038 A1* | 4/2002 | Miller | G16H 50/50 |
| | | | 433/215 |
| 2003/0152884 A1* | 8/2003 | Wiechmann | A61C 7/002 |
| | | | 433/9 |
| 2003/0211444 A1 | 11/2003 | Andrews | |
| 2004/0204787 A1 | 10/2004 | Kopelman et al. | |
| 2006/0115793 A1 | 6/2006 | Kopelman et al. | |
| 2006/0115795 A1 | 6/2006 | Marshall et al. | |
| 2006/0212154 A1* | 9/2006 | Von Schroeter | A61C 9/0046 |
| | | | 715/848 |
| 2008/0131841 A1 | 6/2008 | Taub et al. | |
| 2008/0261165 A1 | 10/2008 | Steingart et al. | |
| 2009/0081617 A1 | 3/2009 | Freeman et al. | |
| 2009/0162813 A1 | 6/2009 | Glor et al. | |
| 2009/0298017 A1 | 12/2009 | Boerjes et al. | |
| 2009/0325125 A1 | 12/2009 | Diangelo et al. | |
| 2010/0241262 A1 | 9/2010 | Taub et al. | |
| 2010/0283781 A1 | 11/2010 | Kriveshko et al. | |
| 2010/0332248 A1* | 12/2010 | Pettersson | G16H 20/40 |
| | | | 705/2 |
| 2011/0038514 A1 | 2/2011 | Weigl | |
| 2011/0196524 A1 | 8/2011 | Giasson et al. | |
| 2011/0196654 A1 | 8/2011 | Genest et al. | |
| 2012/0064489 A1* | 3/2012 | Rubbert | A61L 27/16 |
| | | | 433/175 |
| 2012/0065756 A1* | 3/2012 | Rubbert | A61C 8/0018 |
| | | | 700/98 |
| 2012/0164597 A1 | 6/2012 | McDonald | |
| 2013/0066598 A1* | 3/2013 | Fisker | A61C 19/05 |
| | | | 703/1 |
| 2013/0121479 A1 | 5/2013 | Stephan et al. | |
| 2013/0158694 A1 | 6/2013 | Rubbert et al. | |
| 2013/0309626 A1* | 11/2013 | Arunachalam | A61C 7/28 |
| | | | 433/24 |
| 2013/0317800 A1* | 11/2013 | Wu | G06T 19/20 |
| | | | 703/11 |
| 2014/0105698 A1* | 4/2014 | Vogel | B23F 21/043 |
| | | | 409/36 |
| 2014/0142897 A1* | 5/2014 | Kuo | A61C 7/08 |
| | | | 703/1 |
| 2015/0010881 A1 | 1/2015 | Llop | |
| 2015/0025855 A1* | 1/2015 | Fisker | A61B 6/51 |
| | | | 703/1 |
| 2015/0056576 A1 | 2/2015 | Nikolskiy et al. | |
| 2015/0150660 A1* | 6/2015 | Fisker | A61C 13/0004 |
| | | | 703/1 |
| 2015/0272704 A1 | 10/2015 | Watson et al. | |
| 2016/0242880 A1* | 8/2016 | Nikolskiy | A61C 5/77 |
| 2017/0143457 A1 | 5/2017 | Taub et al. | |
| 2018/0168780 A1 | 6/2018 | Kopelman et al. | |
| 2018/0250102 A1 | 9/2018 | Schulter et al. | |
| 2018/0368956 A1 | 12/2018 | Fisker | |
| 2019/0011996 A1 | 1/2019 | Sabina et al. | |
| 2019/0029524 A1 | 1/2019 | Kopelman et al. | |
| 2019/0029783 A1 | 1/2019 | Wu et al. | |
| 2019/0060036 A1 | 2/2019 | Fisker et al. | |
| 2019/0083208 A1 | 3/2019 | Hansen et al. | |
| 2019/0159863 A1 | 5/2019 | Fisker et al. | |
| 2019/0167391 A1 | 6/2019 | Kopelman | |
| 2019/0209274 A1 | 7/2019 | Barak et al. | |
| 2019/0228501 A1 | 7/2019 | Chang et al. | |
| 2019/0254784 A1 | 8/2019 | Kopelman et al. | |
| 2019/0307539 A1 | 10/2019 | Kopelman et al. | |
| 2020/0197134 A1 | 6/2020 | Llop | |
| 2021/0107272 A1 | 4/2021 | Fisker et al. | |
| 2021/0113089 A1 | 4/2021 | Kopelman et al. | |
| 2021/0304874 A1 | 9/2021 | Nikolskiy et al. | |

FOREIGN PATENT DOCUMENTS

| | | |
|---|---|---|
| EP | 1661529 B1 | 10/2011 |
| EP | 1568335 B1 | 9/2016 |
| EP | 3130311 A1 | 2/2017 |
| EP | 2785272 B1 | 1/2019 |
| WO | 2013092744 A1 | 6/2013 |
| WO | 2014016378 A1 | 1/2014 |
| WO | 2016128828 A1 | 8/2016 |

OTHER PUBLICATIONS

Erik B. Darn, et al., Quaternions, Interpolation and Animation, Technical Report DIKU-TR-98/5, Department of Computer Science, University of Copenhagen, Jul. 17, 1998, in 103 pages.

Mauro Figueiredo, et al., Surface Collision Detection with the Overlapping Bounding Box between Virtual Prototype Models, Researchgate.net/publication/236611862, conference paper Jan. 2003, in 9 pages.

Matt Pharr, et al., Physically Based Rendering: From Theory to Implementation, Chapter 4.3, Bounding Volume Hierarchies, copyright 2004-2019, in 21 pages.

* cited by examiner

702 receiving a digital model comprising a digital dental restoration and a digital preparation tooth

704 digitally determining a virtual insertion path of the digital dental restoration to the digital preparation tooth, the virtual insertion path comprising a plurality of path positions and corresponding digital dental restoration orientations

VIRTUAL DENTAL RESTORATION INSERTION VERIFICATION

RELATED APPLICATIONS

This application is a continuation of, and claims the benefit and priority to, U.S. patent application Ser. No. 16/834,137, filed Mar. 30, 2020, which is hereby incorporated by reference in its entirety.

BACKGROUND

Specialized dental laboratories typically use computer-aided design (CAD) and computer-aided manufacturing (CAM) milling systems to manufacture dental prostheses based on patient-specific instructions provided by dentists.

In a typical work flow, the dental laboratories receive information about a patient's oral situation from a dentist. Using this information, the dental laboratory designs a digital dental prosthesis such as a dental restoration on the CAD system and manufactures the dental restoration on the CAM system with a mill or other fabrication system. While the CAM system or other manufacturing techniques can physically generate the dental restoration, verifying that the dental restoration can be inserted can require physical fabrication of the jaw model and the dental restoration to determine how to insert the dental restoration, which can be time-consuming, expensive, and imprecise.

SUMMARY

A computer-implemented method of digital dental restoration insertion verification includes receiving a digital model having a digital dental restoration and a digital preparation tooth and digitally determining a virtual insertion path of the digital dental restoration to the digital preparation tooth, the virtual insertion path including a plurality of path positions and corresponding digital dental restoration orientations.

A system for digital dental restoration insertion verification, including: a processor, a computer-readable storage medium including instructions executable by the processor to perform steps including: digitally determining a virtual insertion path of the digital dental restoration to the digital preparation tooth, the virtual insertion path including a plurality of path positions and corresponding digital dental restoration orientations.

A non-transitory computer readable medium storing executable computer program instructions for digital dental restoration insertion verification is disclosed, the computer program instructions including instructions for: receiving a digital model comprising a digital dental restoration and a digital preparation tooth and digitally determining a virtual insertion path of the digital dental restoration to the digital preparation tooth, the virtual insertion path including a plurality of path positions and corresponding digital dental restoration orientations.

DETAILED DESCRIPTION

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Although the term "insertion path" is used, it is understood that the same path can also be used to extract the digital dental restoration from its seated position and orientation. In other words, the same path can be used to remove the digital dental restoration.

Figure 1A:
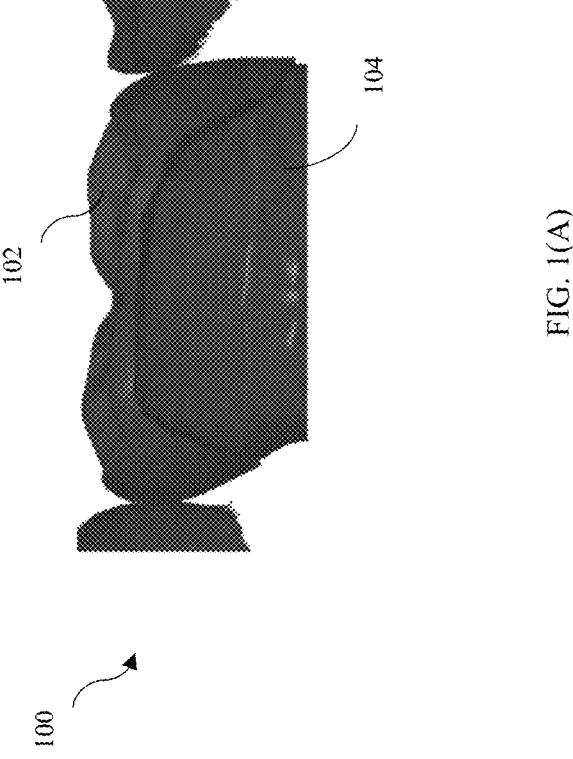
FIG. 1(A) is a front view of a digital model in some embodiments.

FIG. 1(A) illustrates one example of a digital model 100 that can be generated by scanning a physical impression using any scanning technique known in the art including, but not limited to, for example, optical scanning, CT scanning, etc. One example of CT scanning is described in U.S. Patent Application No. US20180132982A1 to Nikolskiy et al., which is hereby incorporated in its entirety by reference. The digital model 100 can also be generated by intraoral scanning of the patient's dentition, for example, as is known in the art. A conventional scanner typically captures the shape of the physical impression/patient's dentition in 3 dimensions during a scan and digitizes the shape into a 3 dimensional digital model. The digital model can include multiple interconnected polygons in a topology that corresponds to the shape of the physical impression/patient's dentition, for example. In some embodiments, the polygons can include two or more digital triangles. In some embodiments, the scanning process can produce STL, PLY, or CTM files, for example that can be suitable for use with a dental restoration design software, such as FastDesign™ dental design software provided by Glidewell Laboratories of Newport Beach, Calif.

In some embodiments, a computer-implemented method of digital dental restoration insertion includes receiving a digital model having a digital dental restoration and a digital preparation tooth and digitally determining a virtual insertion path of the digital dental restoration to the digital preparation tooth, the virtual insertion path including a plurality of insertion path positions and corresponding insertion path orientations. In some embodiments, the insertion path can be collision-free, for example. In some embodiments, the virtual insertion path can be collision-free with respect to the surrounding dentition, for example. In some embodiments, the insertion path can be collision-free with respect to the digital preparation tooth, for example. For example, in some embodiments, the virtual path can include collision-free positions and orientations of the digital dental restoration, for example.

Figure 1B:
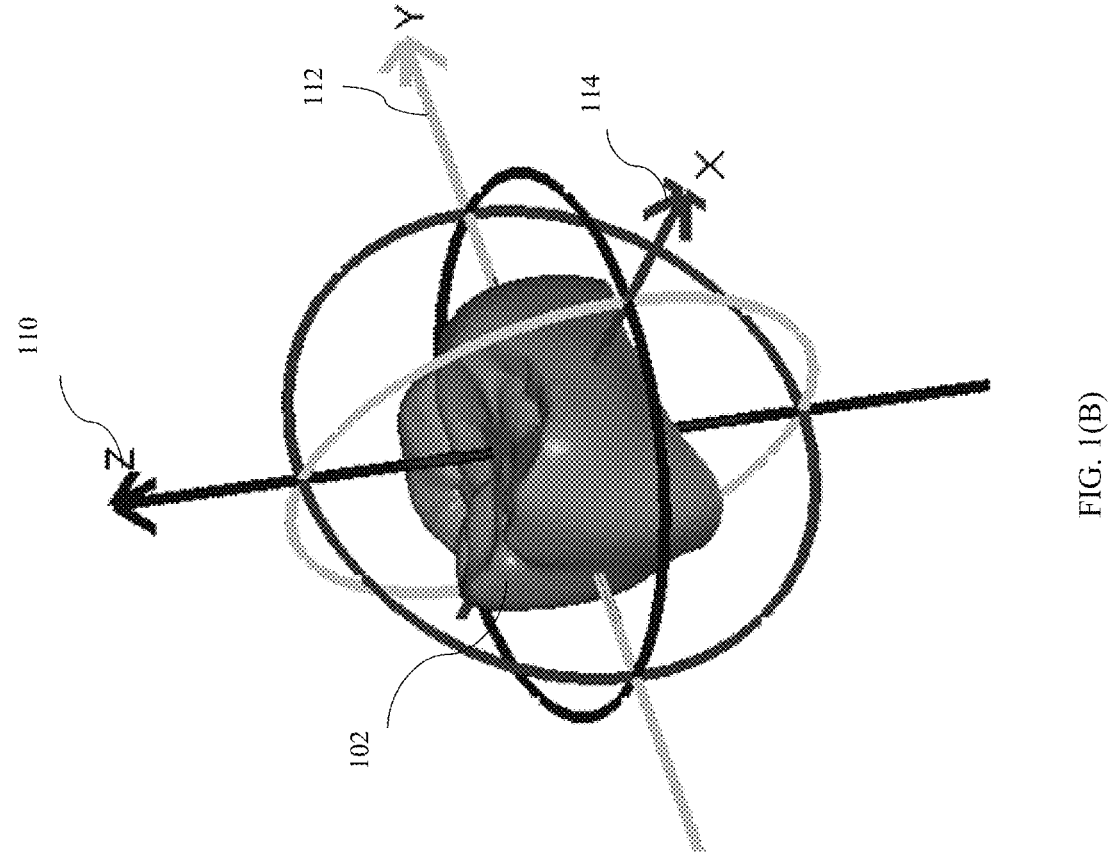
FIG. 1(B) is a perspective view of an example of a digital dental restoration and axes in some embodiments.

FIG. 1(A) illustrates a digital model 100 having a digital dental restoration 102 and a digital preparation tooth 104. The digital preparation tooth 104 can be prepared and the digital dental restoration 102 designed, for example, by a user such as a dentist or dental technician, for example using dental restoration design software such as FastDesign™ or other design software known in the art. The design can include an insertion direction set by the designer of the digital dental restoration, which can differ in different cases in some embodiments, for example. In some embodiments, the insertion direction can be along an occlusal axis, for example. In some embodiments, the insertion direction can be along a long axis of the digital preparation tooth 104, for example. In some embodiments, the digital dental restoration 102 can be a digital crown, a bridge, an inlay, an outlay, or any other digital dental restoration. In some embodiments, the computer-implemented method can receive the digital model, for example, from digital storage or another program as is conventionally known in the art. FIG. 1(B) illustrates axes with respect to the digital dental preparation 102. For example, z-axis 110 can extend along the insertion direction in some embodiments. In some embodiments, the z-axis 110 can extend along an occlusion direction. In some embodiments, the z-axis 110 can extend along the long axis of a tooth. The y-axis 112 and the x-axis 114 can be orthogonal to the z-axis 110, as well as each other.

In some embodiments, the virtual insertion path can include a plurality of insertion path positions and corresponding insertion path orientations. The computer-implemented method can determine the plurality of insertion path positions and orientations in some embodiments, for example, by determining whether the digital dental restoration 102 at several positions and orientations along an insertion direction collides with surrounding dentition and/or the digital preparation tooth 104 (See FIG. 1(A)). The position of the digital dental restoration can be a digital dental restoration center, which can be determined using techniques known in the art, for example. The orientation of the digital dental restoration 102 can be determined, for example, using techniques known in the art. For example, one such technique is described in *Quaternions, Interpolation and Animation* by Erik B. Dam, Martin Koch, and Martin Lillholm, Technical Report DIKU-TR-98/5, Department of Computer Science, University of Copenhagen, Universitetsparken 1 DK-2100 Kbh, Denmark, Jul. 17, 1998, the entirety of which is hereby incorporated by reference. Other techniques known in the art can also be used. Collision detection is known in the art and can be implemented based on searching for intersecting triangles by constructing special search structures for each object, e.g. AABB-trees For example, *Efficient Collision Detection of Complex Deformable Models using AABB Trees* by GINO VAN DEN BERGEN, Department of Mathematics and Computing Science, Eindhoven University of Technology, Nov. 6, 1998 illustrates an example of collision detection, and is hereby incorporated by reference in its entirety. Another example can be found in *SURFACE COLLISION DETECTION WITH THE OVERLAPPING BOUNDING BOX BETWEEN VIRTUAL PROTOTYPE MODELS* by Mauro Figueiredo (Centre for Virtual Environments, University of Salford, University Road, Salford, UK, Escola Superior Tecnologia, Universidade do Algarve, Portugal), and Terrence Fernando, (Escola Superior Tecnologia, Universidade do Algarve, Portugal), *International Conference of Advanced Research in Virtual and Rapid Prototyping*, January 2003, the entirety of which is hereby incorporated by reference. Other collision techniques known in the art can also be used. For example, given two objects in 3D space with their digital surfaces represented as a number of triangles, the computer-implemented method can determine intersection between all triangles from one surface against all triangles from the other surface. If at least one pair of triangles intersect, then two objects collide, otherwise if all pairs of triangles are not intersecting then two objects do not collide.

In some embodiments, if the computer-implemented method detects a collision at a particular position and orientation, the computer-implemented method can shift and/or rotate the digital dental restoration to one or more shifted positions and/or rotated orientations until it determines a collision-free position and orientation. In some embodiments, the computer-implemented method can shift the digital dental restoration by one or more shift step sizes up to a search radius and can optionally rotate the digital dental orientation by one or more rotation steps up to a rotation limit based on the search radius and can determine whether collisions occur at each shift and rotation step. In some embodiments, the computer-implemented method can shift the digital dental restoration along one or more axes other than the z-axis. In some embodiments, the computer-implemented method can rotate along any of the three dimensional axes. In some embodiments, the rotation limit can be a search radius. In some embodiments, the computer-implemented method can designate the collision-free position and orientation as an insertion path position and insertion path orientation. In some embodiments, the computer-implemented method can interpolate between insertion path positions and insertion path orientations to determine the next position and orientation to evaluate for collisions. In some embodiments, a user can specify the shift step size, which can be stored in a configuration file or entered by the user via an input field by the user using a standard Graphical User Interface (GUI) known in the art. The shift step size can be a fixed distance by which to shift the digital dental restoration, for example.

Figure 2A:
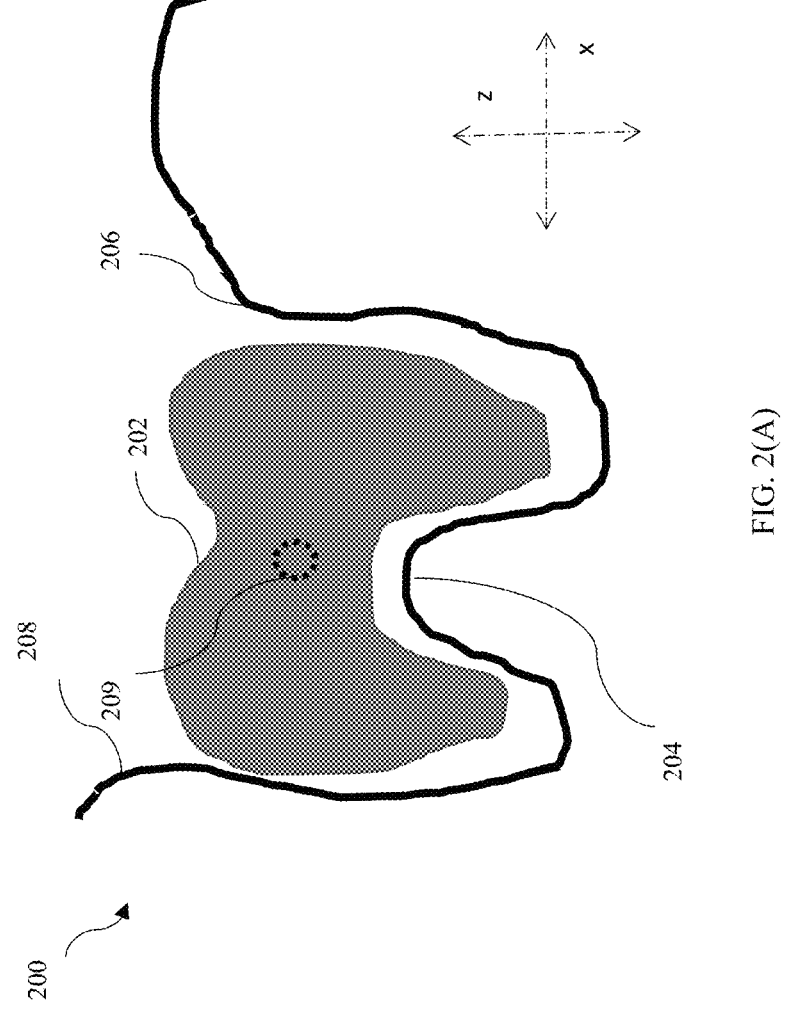
FIG. 2(A) is a cross section view of a digital dental restoration in a seated position in some embodiments.
Figure 2B:
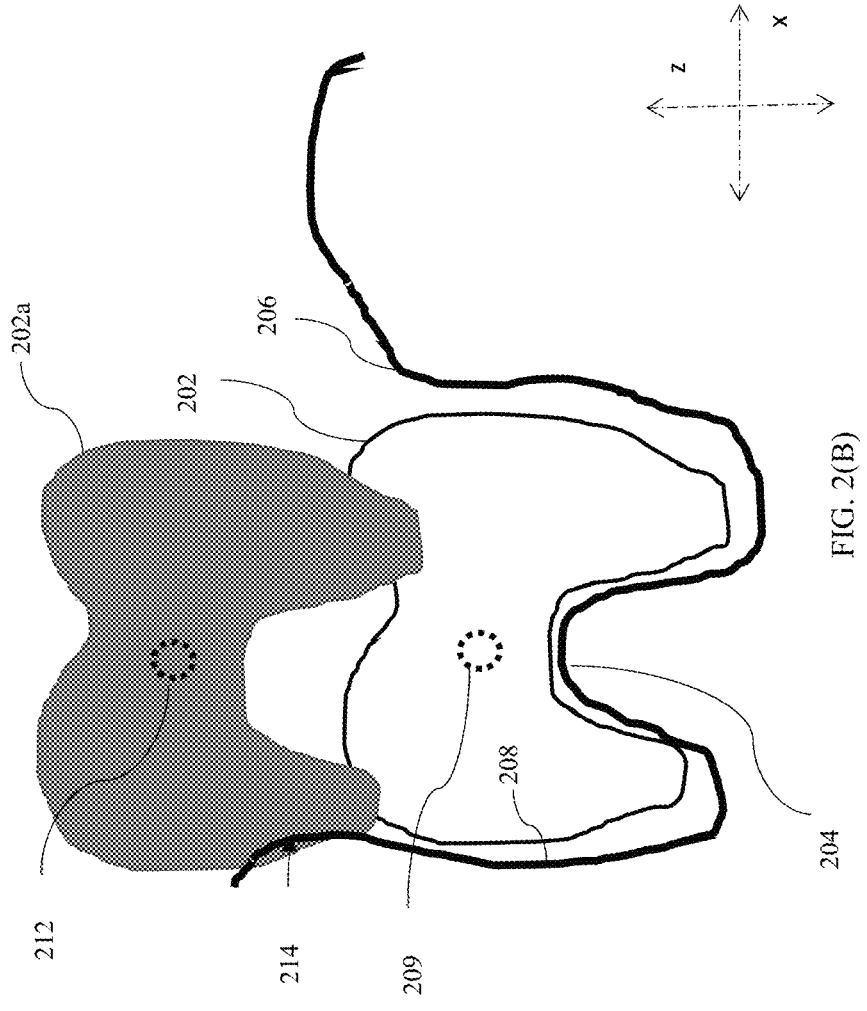
FIG. 2(B) is a cross section view of an illustration of a digital dental restoration in a lifted position in some embodiments.

FIGS. 2(A)-2(B) illustrate one example in some embodiments of the computer-implemented method digitally determining a virtual insertion path. In some embodiments, the virtual insertion path can be collision free, for example. In some embodiments, the virtual insertion path can be collision-free with respect to the surrounding dentition, for example. In some embodiments, the insertion path can be collision-free with respect to the digital preparation tooth, for example. Although the figures are shown in two dimensions (x-axis and z-axis) for simplicity, it is understood that the digital model and elements it includes are three dimensional throughout the disclosure. FIG. 2(A) illustrates a digital model 200 with a digital dental restoration 202, a digital preparation tooth 204 and surrounding dentition. In some embodiments, the computer-implemented method can begin with the digital dental restoration 202 in its seated position and seated orientation as illustrated in FIG. 2(A). The seated position and orientation can be, for example, the designed position and orientation of the digital dental restoration 202 and can be set by the designer or other user of the designing software such as FastDesign or other digital dental restoration software known in the art. The seated position and orientation are the final position and orientation 209 of the digital dental restoration 202 on the insertion path. In the example illustrated in the figure, the surrounding dentition can include, for example, first neighboring tooth 206 and second neighboring tooth 208. The computer-implemented-method can determine whether any collisions occur between the digital dental restoration 202 in its final position and orientation 209 and the surrounding dentition and/or the digital preparation tooth 204. If the computer-implemented method determines no collisions occur between the digital dental restoration 202 and the surrounding dentition and the digital preparation tooth 204, then the computer-implemented method can proceed to evaluate the next position. If, however, the computer-implemented detects any collisions at the final position and orientation 209, then the computer-implemented method stops processing in some embodiments. Checking for collisions in the final position and orientation 209 can advantageously, for example, catch design errors and avoid generating an insertion path for an unseatable dental restoration.

Provided no collisions occur in the final position and orientation 209 of the digital dental restoration 202, the computer-implemented method can determine an initial position and orientation along the insertion direction. FIG. 2(B) illustrates an example of the computer-implemented method determining an initial position and orientation of digital dental restoration virtual insertion path in some embodiments. As illustrated in the figure, the computer-implemented method can determine a lifted position 212 of the digital dental restoration 202 from the final position 209 along the z-axis which in some embodiments can be along the insertion direction or along an occlusal axis, or the long axis of the digital preparation tooth, for example. The lifted position 212 can be any distance from the final position 209. In some embodiments, for example the lifted position can be up to 6 mm from the final position 209. Other lifted position values can be used. In some embodiments, the lifted orientation is the same as the final orientation.

In some embodiments, the computer-implemented method can determine whether any collisions occur between the digital dental restoration 202a and surrounding dentition (such as the first neighboring tooth 206 and/or second neighboring tooth 208) or the digital preparation tooth 204 at the lifted position 212. If no collisions occur, the computer-implemented method can determine the initial position and orientation as the lifted position 212 and orientation and then determine.

If, however, one or more collisions occur, then the computer-implemented method can shift the digital dental restoration 202a along the x-axis and/or y-axis and optionally rotate the digital dental restoration 202a around the x-axis, the y-axis, and/or the z-axis. In the example of FIG. 2(B), a collision occurs in a first collision surface region 214 as illustrated at the lifted position 212 (along the z-axis). The computer-implemented method can evaluate only those shift positions of the digital dental restoration 212a on the x, y axes in which a maximum displacement of the digital dental restoration 212a surface points to the particular shift position is within the user-configurable search radius. In the case of only shifting (no rotation), each digital surface point is displaced by the same amount to its shifted position. Accordingly, the computer-implemented method can determine the displacement of any digital surface point as the maximum displacement in the case of shifting only. If the maximum displacement is greater than the user-configurable search radius, then the computer-implemented method does not utilize the shift position. If, on the other hand, the computer-implemented method determines the maximum displacement is within the user-configurable search radius, then the shift position is utilized to evaluate collisions at the shift position. One advantage of a limiting search radius can include, for example, reducing the number of shifts to consider, thereby improving speed, for example. One advantage of a limiting search radius can also include, for example, eliminating large shifts that may cause collisions, for example.

In some embodiments, the digital dental restoration can be represented by a bounding volume such as for example, a sphere or a parallelpiped, or other suitable volume that tightly encloses the restoration. Bounding volumes are known in the art such as described in, for example, *Physically Based Rendering: From Theory To Implementation*, Chapter 4.3, by Matt Pharr, Wenzel Jakob, and Greg Humphreys, © 2004-2019, the entirety of which is hereby incorporated by reference. In some embodiments, for example, the computer-implemented method can determine the maximum displacement of surface points on the surface of the bounding volume.

Figure 3A:
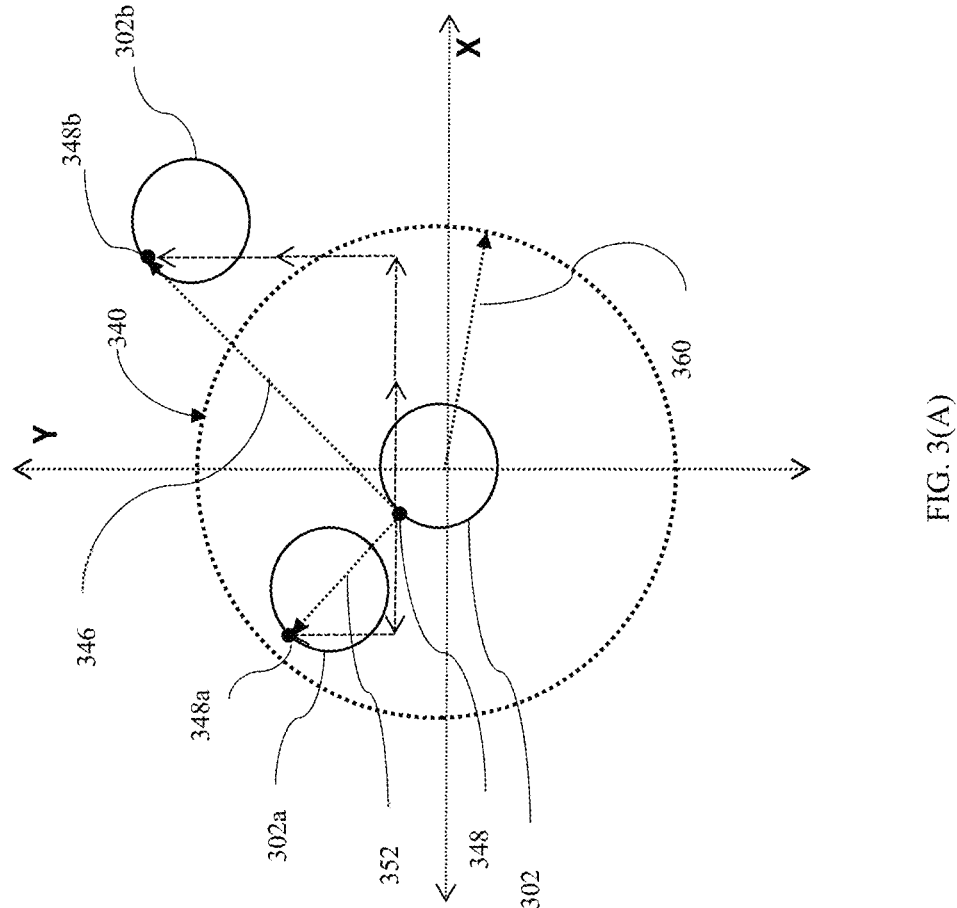
FIG. 3(A) is a top view of an illustration of a digital dental restoration and shift positions in some embodiments.

FIG. 3(A) illustrates an example of determining shift positions within the search radius. As illustrated in the figure, a digital dental restoration 302 is arranged at a particular position on the z-axis and can be shifted to different positions along the x-axis and the y-axis. Two shift positions such as first shift position 302a and second shift position 302b are illustrated for clarity; many more shift positions are possible. First shift position 302a illustrates an example of shifting the digital dental restoration 302 by one negative shift step size along the x-axis and one positive shift step size along the y axis. The first shift position 302a displaces a digital surface point 348 of the digital dental restoration 302 to a position 348a with a displacement distance 352. Since the first shift position 302a involves only shifting (no rotation), all digital surface points of the digital dental restoration 302 are displaced by the same amount. The maximum displacement at first shift position 302a is therefore the displacement distance 352. The computer-implemented method can determine that the maximum displacement (displacement distance 352) is less than the search radius 360 (search perimeter 340), and can therefore include the first shift position 302a as a shift position to evaluate for collisions. Also illustrated in the figure is a second shift position 302b. Second shift position 302b illustrates an example of shifting the digital dental restoration 302 by two positive shift step sizes along the x-axis and two positive shift step sizes along the y axis. The second shift position 302b displaces the digital surface point 348 of the digital dental restoration 302 to a position 348b with a displacement distance 346. Since the second shift position 302b involves only shifting (no rotation), all digital surface points of the digital dental restoration 302 are displaced by the same amount in the second shift position. The maximum displacement of all points at second shift position 302b is therefore the displacement distance 346. The computer-implemented method can determine that the maximum displacement (displacement distance 346) is greater than the search radius 360, and can therefore excludes the second shift position 302b as a potential shift position to evaluate for collisions. As an example, if a search radius is 4 mm and shift step size is 400 microns, then the computer-implemented method can determine as an example, whether collisions occur at positions:

Shift along X on ±4 mm,

Shift along Y on ±4 mm,

Shift along X on ±1 mm and shift along Y on ±3.6 mm. This is within the search radius because 1*1+3.6*3.6<4*4.

Shift along X on ±3 mm and shift along Y on ±2.4 mm. This is within the search radius because 3*3+2.4*2.4<4*4.

In some embodiments, the computer-implemented method can rotate the digital dental restoration 202a around the x-axis, y-axis, and/or z-axis to determine a collision-free orientation. (See FIG. 1(B)). In some embodiments, the computer-implemented method can perform rotation incrementally by one or more rotation steps, for example. In some embodiments, a rotation step value can be, for example the (shift step size)/(digital dental restoration radius) radians. In some embodiments, the restoration radius can be that of the bounding volume of the digital dental restoration, for example. In some embodiments, the computer-implemented method can perform rotations such that the maximum displacement of digital surface points is within the search radius. Where rotation is involved, the computer-implemented method can determine the displacement of each digital surface point of the digital dental restoration or its bounding volume as its (distance to the rotation axis)*(the angle of rotation in radians). In some embodiments, the computer-implemented method can determine one or more rotational positions as those falling within the user-configurable search radius. The computer-implemented method can determine the maximum displacement of one or more digital surface points at each rotation step and evaluate only those rotation steps whose maximum displacement is less than the search radius. One advantage of a limiting search radius can include, for example, minimizing the number and extent of rotations to consider, thereby improving speed, for example. One advantage of a limiting search radius can also include, for example, eliminating large rotations that may cause collisions, for example.

Figure 3B:
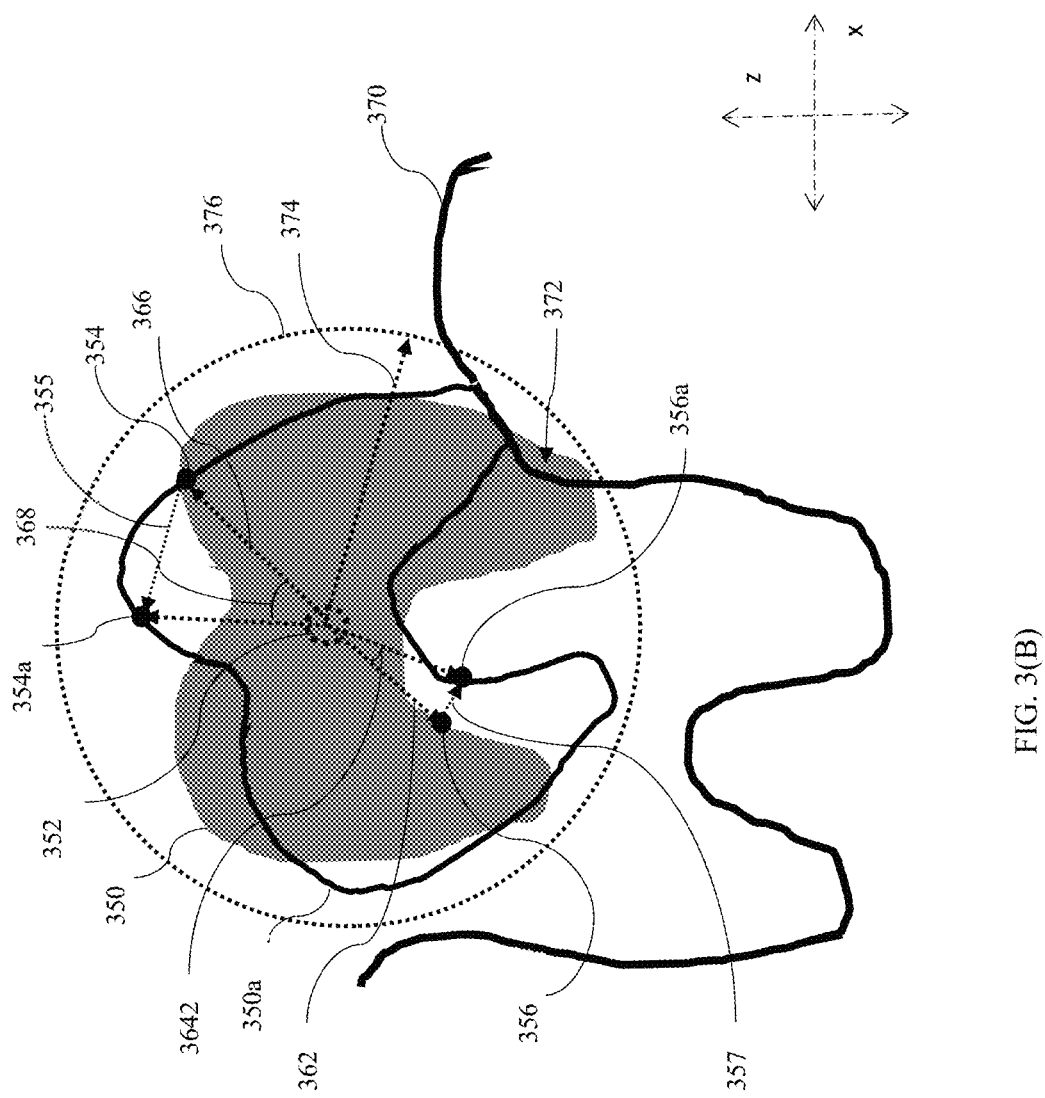
FIG. 3(B) is a cross section view example illustration of a rotated digital dental restoration in some embodiments.

For example, FIG. 3(B) illustrates an example of rotation around y-axis 352 with the digital dental restoration 350. As illustrated in the figure, the digital dental restoration 350 collides at the shifted position with surrounding dentition such as, for example, first neighboring tooth 370 in digital surface region 372. As illustrated in the example shown in the figure, the computer-implemented method can determine rotation positions that fall within a search radius 374 (defining a sphere such as sphere 376, shown as a circle in two dimensions in the figure for clarity). For example the computer-implemented method can determine a first rotated position 350a in which the digital dental restoration 350 is rotated around y-axis 352. The first rotated position can be determined as the (shift step size)/(digital dental restoration or bounding volume radius). The computer-implemented method can determine displacement of digital surface points from the rotation in some embodiments, and determine the maximum displacement. For example, in the figure, the computer-implemented method can determine a first digital surface point 356 undergoes a displacement 357 to a rotated position 356a by multiplying its distance to the y-axis 362 with the angle 364. Similarly, the computer-implemented method can determine a digital surface point 354 undergoes a displacement 355 to a rotated position 354a by multiplying its distance to a y-axis 366 with the angle 368. The computer-implemented method can repeat this for additional digital surface points, including all digital surface points. The computer-implemented method can determine the maximum displacement of one or more digital surface points. For example, the computer-implemented method can determine the displacement 355 of digital surface point 354 is greater than the displacement 357 of digital surface point 356. In the example, the computer-implemented method can determine that the displacement 355 is less than the search radius 374 and determine that the first rotation position 350a is within the search radius 374.

The computer-implemented method can similarly determination additional rotational positions within the search radius and determine whether collisions occur at each rotational position. In the example of FIG. 3(B), the digital dental restoration 350 at first rotated position 350a does not encounter any collisions, for example. The computer-implemented method can determine that the digital dental restoration 350 at the position and orientation is part of the insertion path.

In some embodiments, the computer-implemented method can perform shifting and/or rotating within the search radius in any combination of shifts and rotations until it determines a collision-free shift position and orientation of the digital dental restoration. In some embodiments, the computer-implemented method can determine collisions at each shift step size and/or each rotational step. In some embodiments, the computer-implemented method can determine shifted positions and rotations to consider in parallel using a multi-core processor, for example. In some embodiments, the computer-implemented method can also determine collisions in parallel at one or more position and orientation combinations. This can, for example, advantageously utilize multi-core processors to consider a large number of position and orientation combinations at the same time, thereby improving processing time and allowing more complex combinations of shifts and rotations.

In some embodiments, the computer-implemented method can multiply the shift step size by a shift step size adjustment factor between different combinations to lessen many movements due to many degrees of freedom. In some embodiments, the shift step size adjustment can be a noninteger and not on the same number twice. This can, for example, advantageously minimize or avoid testing the same movement several times. The following is an example for illustrative purposes only, and is not intended to limit the scope of the disclosure in any manner. For example, given the following 1. ShiftX—Shift of the restoration along X (plus or minus) by shift step size
2. ShiftY—Shift of the restoration along Y (plus or minus) by shift step size
3. ShiftZ—Shift of the restoration along Z (plus or minus) by shift step size
4. RotX—Rotation of the restoration around X (plus or minus) on rotational step equal to shift step size divided by average restoration radius in radians.
5. RotY—Rotation of the restoration around Y (plus or minus) on same rotational step
6. RotZ—Rotation of the restoration around Z (plus or minus) on same rotational step The computer-implemented method can, in the example, construct the following shifts and rotation steps (movements):

subset $A$=[ShiftX,ShiftY], by given shift step size subset $B$=[ShiftX,ShiftY,RotX], by shift step size= (first shift step adjustment)*given shift step size subset $C$=[ShiftX,ShiftY,RotY], shift step size=(second shift step adjustment)*given shift step size subset $D$=[ShiftX,ShiftY,RotZ], shift step size=(third shift step adjustment)*given shift step size subset $E$=[ShiftX,ShiftY,RotX,RotY,RotZ], step size= (fourth shift step adjustment)*given shift step size In the example, the computer-implemented method can test collisions first without shifting/rotating, then movements from subset A, then movements from subsets B, C, D, and E. In the example, the computer-implemented method can adjust the shift step size in subsets B, C, D, E based on a shift step adjustment. In the example, the first shift step adjustment can be 2.5, the second shift step size adjustment can be 2.1, the third shift step size adjustment can be 2.3, and the fourth shift step size adjustment can be 3.8 for example.

The computer-implemented method can, as illustrated in the example, test collisions at different positions and/or orientations and select the first movement in which no collisions occur and determine that x-y axis position and orientation as part of the insertion path at that particular position along the z-axis. One advantage can include, for example, increased speed in processing. In some embodiments, the computer-implemented method can attempt shifting first along the x-axis and/or y-axis and then perform shifting in combination with rotating around one or more axes, for example. In some embodiments, the computer-implemented method can perform smaller shifts and rotations before larger ones, for example. In some embodiments, shifting and rotating are performed independently of one another. One advantage can include, for example, flexibility in determining positions and orientations evaluated during collision detection such as, for example, performing smaller, simpler movements first and then performing more complex movements only if necessary to determine the collision-free position and orientation. The computer-implemented method can utilize any combination of shifting along the x-axis and/or the y-axis and rotating around the x-, y-, and/or z-axis at a particular z-axis position and determine a collision-free position in some embodiments.

In some embodiments, the computer-implemented method can determine whether any collisions occur between the digital dental restoration and surrounding dentition and/or the digital preparation tooth occur at one or more shifted positions and/or one or more rotated orientations. In some embodiments, if collisions with the surrounding dentition and/or preparation tooth occur, the computer-implemented method can repeat shifting incrementally by one or more shift step sizes and/or rotating by one or more rotational steps to determine a collision-free position and orientation of the digital dental restoration. If no collisions occur between the digital dental restoration at a shifted position and orientation, the computer-implemented method can designate the shifted position and orientation as part of the insertion path.

In some embodiments, the computer-implemented method can determine whether any collisions occur at one or more shift positions and one or more rotations. One or more advantages of shifting and rotating as disclosed can include, for example, faster processing times since more complex movements are performed only if simpler movements do not provide a collision-free position and orientation of the digital dental restoration. In some embodiments, if the computer-implemented method determines no collision-free position and orientation, the computer-implemented method provide one or more digital surface collision regions.

In some embodiments, the computer-implemented method can determine a next intermediate z-axis position and orientation by performing one or more interpolations. For example, upon determining a collision free x-y axis position and orientation at a particular position on the insertion path, the computer-implemented method can determine one or more intermediate positions and orientations between two or more insertion path positions. In some embodiments, the computer implemented method can determine an intermediate position by linear interpolation as is known in the art. In some embodiments, the computer-implemented method can perform linear interpolation on a digital dental restoration center. The computer-implemented method can determine the digital dental restoration center in some embodiments using techniques known in the art such as, for example, determining a mean value of all restoration triangle centers taken with weights equal to the areas of corresponding triangles.

In some embodiments, the computer-implemented method can perform linear interpolation on the digital dental restorations as follows. Given a first digital dental restoration center position s0 and second digital dental restoration center position s1 on the insertion path and the amount of interpolation t is in [0, 1], the computer-implemented method can determine an intermediate shift as:

$$\text{Lerp}(s_0,s_1,t)=(1-t)*s_0+t*s_1.$$

In some embodiments, the computer-implemented method can determine an intermediate orientation as follows. Given two orientations represented by unit quaternions $p_0$ and $p_1$ and the amount of interpolation t is in [0, 1], the interpolated intermediate orientation can be determined by the quaternion:

$$\text{Slerp}(p_0, p_1; t) = \frac{\sin[(1-t)\Omega]}{\sin\Omega}p_0 + \frac{\sin[t\Omega]}{\sin\Omega}p_1.$$

where $\cos \Omega$ is equal to dot product of $p_0$ and $p_1$. Linear and spherical interpolation are known in the art and described in, for example, *Quaternions, Interpolation and Animation* described previously and incorporated by reference.

Figure 4A:
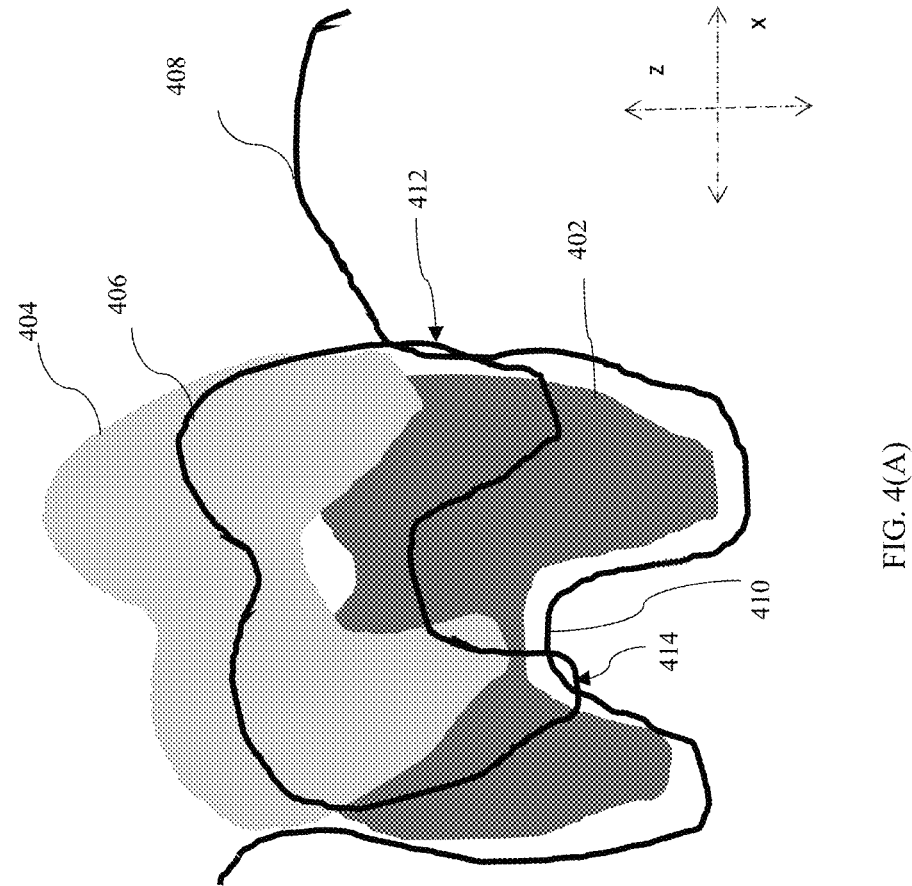
FIG. 4(A) is a cross section view of illustration of an example of interpolation in some embodiments.

FIG. 4(A) illustrates an example of interpolation. The example includes a digital dental restoration at a seated position and orientation 402 and the digital dental restoration at a first insertion path position and orientation 404. The digital dental restoration at the first insertion path and orientation 404 can be one the computer-implemented method shifted and/or rotated as described in the present disclosure to determine a collision-free position and orientation. In some embodiments, the computer-implemented method can interpolate between the digital dental restoration at the seated position and orientation 402 and the digital dental restoration at the first insertion path position and orientation 404 to determine the digital dental restoration at a first intermediate position 406, for example.

In some embodiments, the computer-implemented method can perform collision detection on intermediate positions as described previously. For example, as illustrated in the figure, the computer-implemented method can determine that the digital dental restoration at the first intermediate position 406 collides with surrounding dentition such as first neighboring tooth 408 and digital preparation tooth 410, with collision regions 412 and 414, respectively. In some embodiments, the computer-implemented method can shift and/or rotate the digital dental impression at one or more intermediate positions such as the intermediate position 406 as described in the present disclosure to determine a collision-free position and orientation. In some embodiments, the computer-implemented method can perform shifting along the x and/or y axis(es), and can perform rotations around the x, y, and/or z-axis as described in the present disclosure. The computer-implemented method can designate a collision-free position and orientation of the intermediate position and orientation 406 as part of the insertion path.

In some embodiments, the computer-implemented method can perform one or more interpolation steps to determine intermediate positions and orientations. One advantage of performing one or more interpolation steps can include, for example, catching positions along the insertion direction that may cause collisions, and shifting the position and/or rotating the orientation of the digital dental impression to determine a collision-free position and orientation. In some embodiments, the computer-implemented method can determine shift positions and orientations within the search radius at each intermediate position in the particular interpolation step to determine collision-free positions and orientations as described previously. In some embodiments, the number of interpolation steps can be a user-configurable value. In some embodiments, for example, the number of interpolation steps can be set to 8 (or any other value) by setting the number of insertion path segments to 256 segments ($2^8$), for example. If the lifted position is 6 mm, as an example, then each segment can be approximately 0.02 mm, for example. More or fewer segments are possible by changing the user-configurable interpolation step value. In some embodiments, the computer-implemented method can automatically adjust the search radius with each interpolation step. For example, in some embodiments, the computer-implemented method can automatically adjust the search radius value in each interpolation step to half of the previous search radius value. One advantage of adjusting the search radius value can include, for example, reducing the chances of collision by keeping shifts and/or rotation small along intermediate positions where collisions occur. One advantage of adjusting the search radius can also include, for example, a smooth insertion path. One advantage of adjusting the search radius can include, for example, that the positions/orientations can change by smaller amounts in close positions on the path.

Figure 4B:
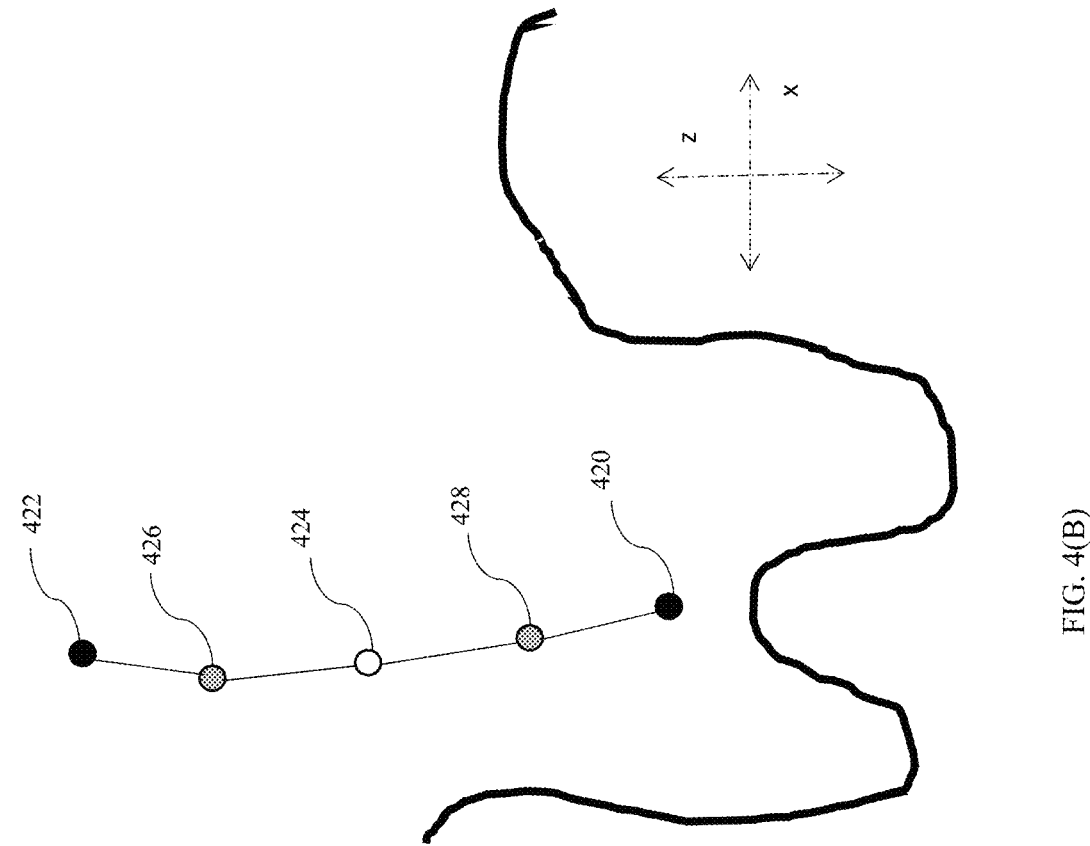
FIG. 4(B) is a cross section view of an illustration of interpolation in some embodiments.

For example, as illustrated in FIG. 4(B), the computer-implemented method can in a first interpolation interpolate between a digital dental restoration in a seated position and orientation 420 and a collision-free lifted position and orientation 422 to determine a first intermediate position and orientation 424. In some embodiments, the computer-implemented method can determine a collision-free first intermediate position by shifting and rotating within a first interpolation search radius as described previously. The first interpolation search radius can be, in some embodiments, ½ of the search radius set by the user, for example. In a second interpolation, the computer-implemented method can interpolate between collision-free lifted position and orientation 422 and the collision-free first intermediate position and orientation 424 to determine second intermediate position and orientation 426 in some embodiments, for example. Also in the second interpolation, the computer-implemented method can interpolate between the collision-free first intermediate position and orientation 424 and the seated third intermediate position and orientation 428 to determine third intermediate position and orientation 428 in some embodiments, for example. In some embodiments, the computer-implemented method can determine collision free positions and orientations within a second interpolation search radius for the second intermediate position and orientation 426 and the third intermediate position and orientation 428. In some embodiments, the computer-implemented method can adjust the second interpolation search radius to ½ of the first interpolation search radius (or ¼ of the search radius) when determining collision-free positions and orientations of the digital dental restoration at the second intermediate position and orientation 426 and the third intermediate position and orientation 428. For example, if the search radius is set to 4 mm, then the computer-implemented method can evaluate shift positions and orientations around the first intermediate position and orientation 424 up to 2 mm search radius after the first interpolation. After the second interpolation, the computer-implemented method can evaluate shift positions and orientations around the second intermediate position and orientation 426 and third intermediate position and orientation 428 up to a 1 mm search radius.

In some embodiments, the computer-implemented method can determine intermediate positions and orientations between collision-free positions and orientations.

Figure 5:
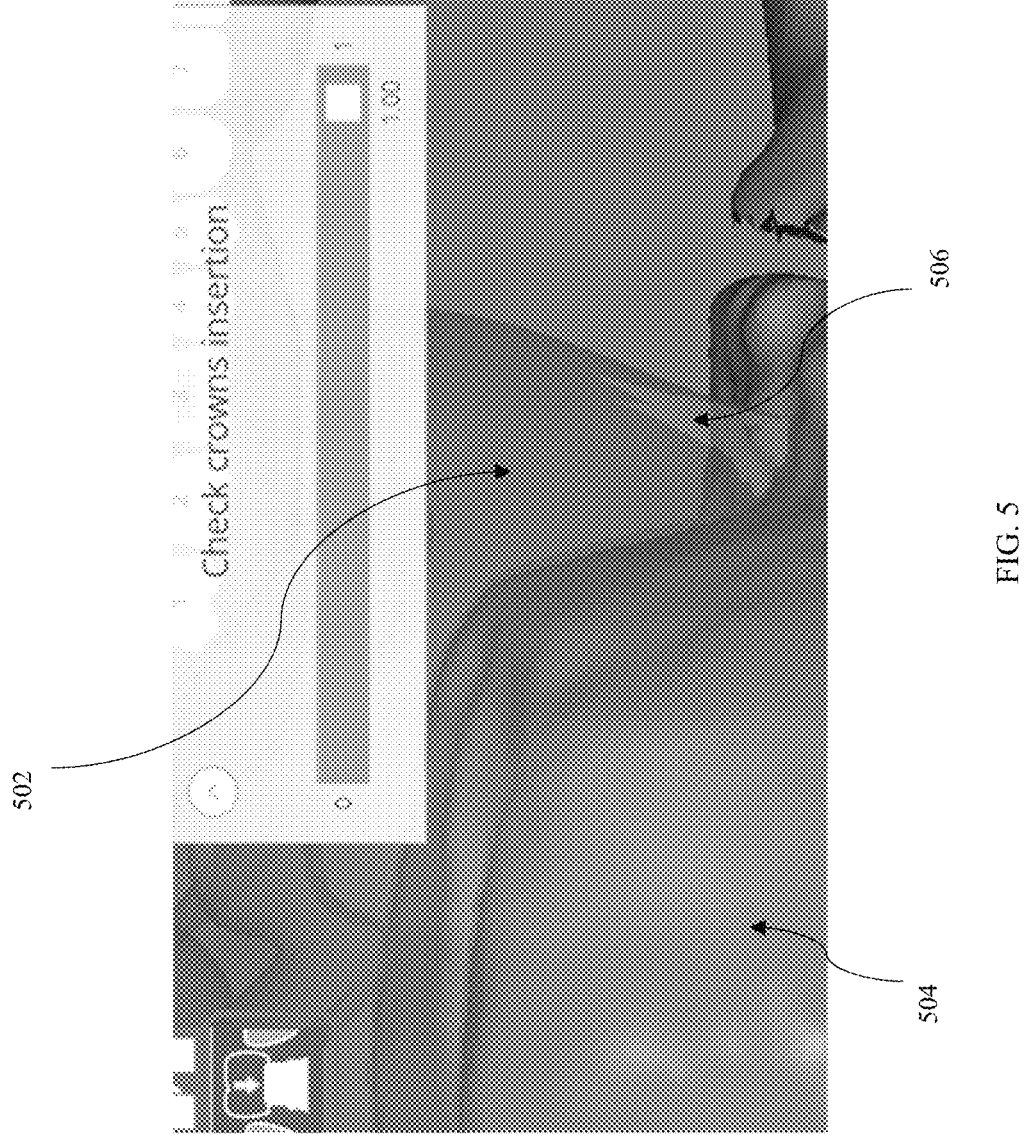
FIG. 5 is a front view of a digital model with at least one collision region in some embodiments.

In some embodiments, the computer-implemented method may not find a collision-free position and orientation within the search radius at a particular point on the z-axis. In some embodiments, the computer-implemented method can, for example, stop searching in such a case. In some embodiments, the computer-implemented method can display the colliding position on a display along with any digital preparation tooth digital surface triangles and/or neighboring tooth digital surface triangles involved in the collision as illustrated in the example shown in FIG. 5. In FIG. 5, digital dental restoration 502 is in a position and orientation over digital preparation tooth 504, for example. The computer-implemented method determines that no shift and/or rotational combinations of the digital dental restoration at its position and orientation are without collisions. For example, the digital dental restoration collides with a neighboring tooth (not shown) in a collision region 506. The computer-implemented method can output the digital preparation tooth 504, the digital dental restoration 502 and the collision region 506 on a display in some embodiments, for example. In some embodiments, the computer-implemented method can determine any subsequent intermediate positions and orientations through interpolation, but skip determining whether those positions and orientations are collision-free. In this way, the computer-implemented method can determine an insertion path despite collisions, and display the collision information on a display. One advantage can include, for example, providing a user with information regarding which region(s) to adjust to remove the collision.

In some embodiments, the computer-implemented method can determine the insertion path as described in the present disclosure with an adjusted digital dental restoration that can take into account any tolerances. Any features disclosed herein with respect to the digital dental restoration can apply to/be used with the reduced digital dental restoration. Tolerances can include any deviations between a designed digital dental restoration and its physical counterpart. For example, in some embodiments, tolerances can include those arising from scanning and/or manufacturing deviations/imprecisions. The manufacturing and/or scanning tolerance ranges can be determined from the scanning and/or manufacturing equipment used. In some embodiments, the tolerance value can range from 30 microns to 140 microns, for example. In some embodiments, the tolerance can be set to zero, meaning the digital dental restoration will not be reduced. In some embodiments, the computer-implemented method can adjust the digital dental restoration to compensate. For example, in some embodiments, the computer-implemented method can reduce designed digital dental restoration in size prior to determining the insertion path. For example, in some embodiments, the computer-implemented method can reduce in size in at least one or more digital dental restoration regions to accommodate any tolerances.

Figure 6:
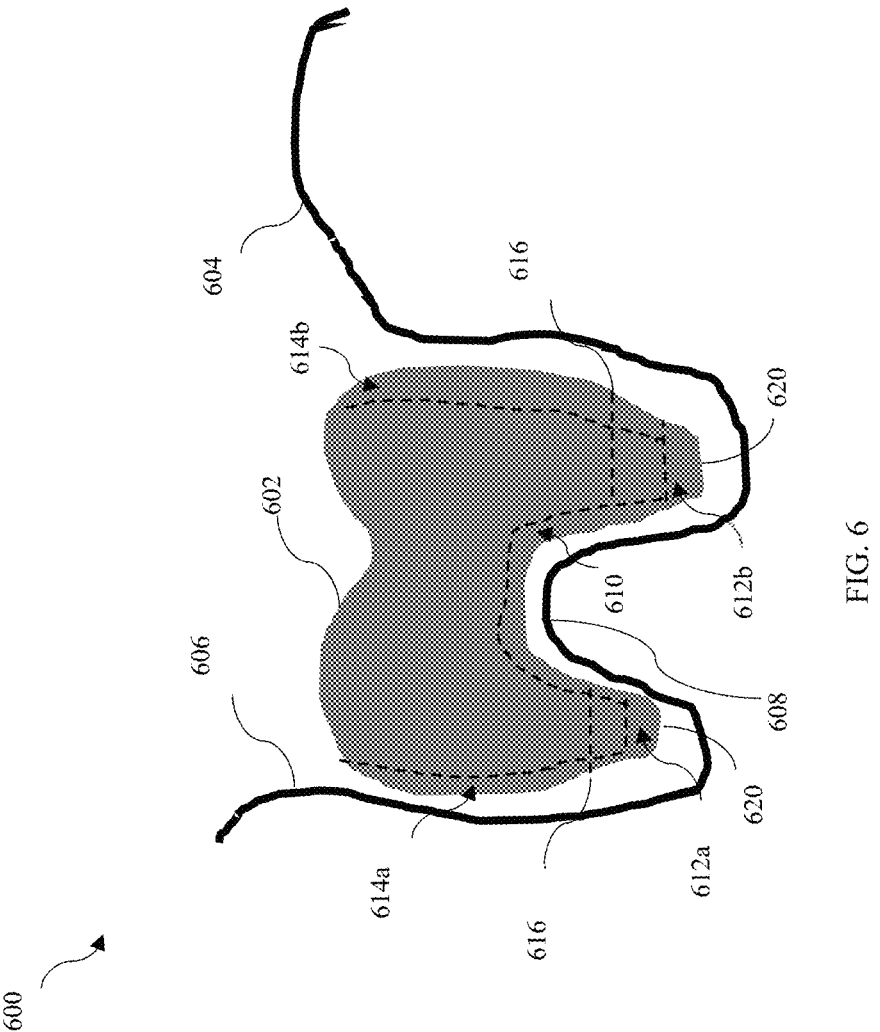
FIG. 6 is a cross section view of an illustration of reducing a digital dental restoration in some embodiments.

FIG. 6 illustrates a digital model 600 of a designed digital dental restoration 602 with first neighboring digital tooth 604, second neighboring digital tooth 606, and digital preparation tooth 608. In some embodiments, for example, the computer-implemented method can reduce an inner digital surface region 610, a digital margin band 612a on the side of the second neighboring digital tooth 606, a digital margin band region 612b on the side of the first neighboring digital tooth 604, an outer digital surface region 614a on the side of the second neighboring digital tooth 606, and an outer digital surface region 614b on the side of the first neighboring digital tooth 604. The inner surface region 610 is the digital surface region that interfaces with the digital preparation tooth 608.

In some embodiments, the computer-implemented method can reduce the inner surface region 610 and the digital margin band regions 612a and 612b by a digital preparation tooth 608 tolerance. In some embodiments, this can be the tolerance from manufacturing and/or scanning the preparation tooth. As an example, in some embodiments, this value can be up to 30 microns, for example. In some embodiments, the computer-implemented method can reduce the outer digital surface regions 614a and 614b by a neighboring tooth contact tolerance. In some embodiments, the neighboring tooth contact tolerance can be, for example, up to 100 microns. In some embodiments, the computer-implemented method can at a threshold region 616 measured from a margin line 620 taper the reduction amount from the outer digital surface regions 614a and 614b toward the margin line 620. In some embodiments, the computer-implemented method can taper the reduction amount proportionately from the neighboring tooth contact tolerance value to the digital preparation tooth tolerance value from the threshold region 616 to the margin line 620. In some embodiments, the threshold region 616 can be up to 1 mm from the margin line 620, for example. In some embodiments, the digital margin band is a closed band (regions 612a and 612b shown because the figure is shown as a cross section) and can have a thickness range from 0.1 mm to 1 mm, for example. In some embodiments, the computer-implemented method can, given a point on an outer surface of the digital dental restoration, determine its distance to the margin line 620, for example. If the point is further than the threshold region 616—such as more than 1 mm from the margin line, for example—then the reduction value there is the neighboring tooth contact tolerance such as, for example, 100 microns. If the distance is less than the threshold region 616—such as, for example, less than 1 mm from the margin line, 620, then the reduction value is proportional to this distance in between 30 microns and 100 microns, for example. In some embodiments, the computer-implemented method can reduce the digital preparation tooth 608 size, the first neighboring digital tooth 604 size, and/or the second neighboring digital tooth size 606, or any combination thereof, for example instead of or in conjunction with reducing the digital dental restoration 602.

One advantage of using an adjusted digital dental restoration to determine the insertion path as described in the present disclosure can include taking into account tolerances introduced by physical processing of the digital dental restoration such as manufacturing and/or scanning. These tolerances can be taken into account using collisions between digital surfaces rather than calculating interpenetration depths, which can be computationally slow. Another advantage can include, for example, ignoring shallow collisions between the designed digital dental restoration and surrounding dentition, and/or the digital preparation tooth, for example.

In some embodiments, the computer-implemented method can utilize a bounding volume in place of the digital dental restoration radius. In some embodiments, the shifting and rotation are limited by a user-configurable search radius, which in 3 dimensions can be, for example, a search sphere. The computer-implemented method in some embodiments can consider only shift distances and rotations such that the digital dental restoration or its bounding volume surface is within the search sphere.

Figure 7:
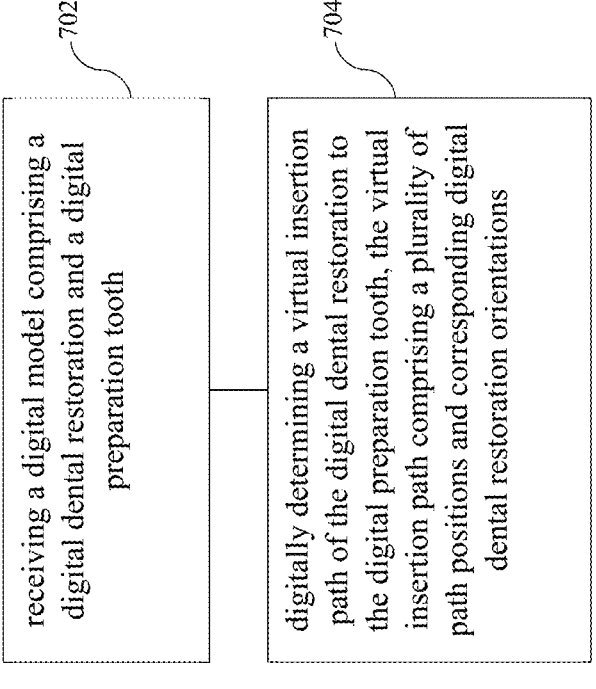
FIG. 7 is a flow chart illustrating a computer-implemented method in some embodiments.

FIG. 7 illustrates an example of a computer-implemented method with one or more features in some embodiments, The computer-implemented method can include receiving a digital model comprising a digital dental restoration and a digital preparation tooth at 702 and digitally determining a virtual insertion path of the digital dental restoration to the digital preparation tooth, the virtual insertion path comprising a plurality of path positions and corresponding digital dental restoration orientations at 704.

The method can include one or more optional features in any combination. For example, the collision-free virtual insertion path can be within a tolerance. The tolerance can be one or more selected from the group consisting of a manufacturing tolerance and a scanning tolerance. One or more regions of the digital dental restoration can be reduced in size based on the tolerance. The tolerance can be a user-configurable value. The method can an also include flagging the digital dental restoration when virtual insertion path is not within the tolerance. An initial virtual insertion path position of the virtual insertion path can start from a lifted position and can terminate on the digital preparation tooth. Determining the virtual insertion path can include interpolating one or more intermediate digital dental restoration positions and corresponding digital dental restoration orientations from the lifted position to the digital preparation tooth. The one or more intermediate digital dental restoration positions and corresponding intermediate digital dental restoration orientations can be free of collisions with surrounding dentition. The lifted position and the corresponding lifted orientation can be free of collisions with surrounding dentition. Determining the virtual insertion path can be performed automatically by the computer-implemented method. The digital dental restoration can be one or more selected from the group consisting of a digital crown, a bridge, an inlay, and an outlay. The virtual insertion path can be collision-free. The virtual insertion path can be collision-free with surrounding digital dentition. The virtual path can be collision-free with the digital restoration tooth.

Figure 8:
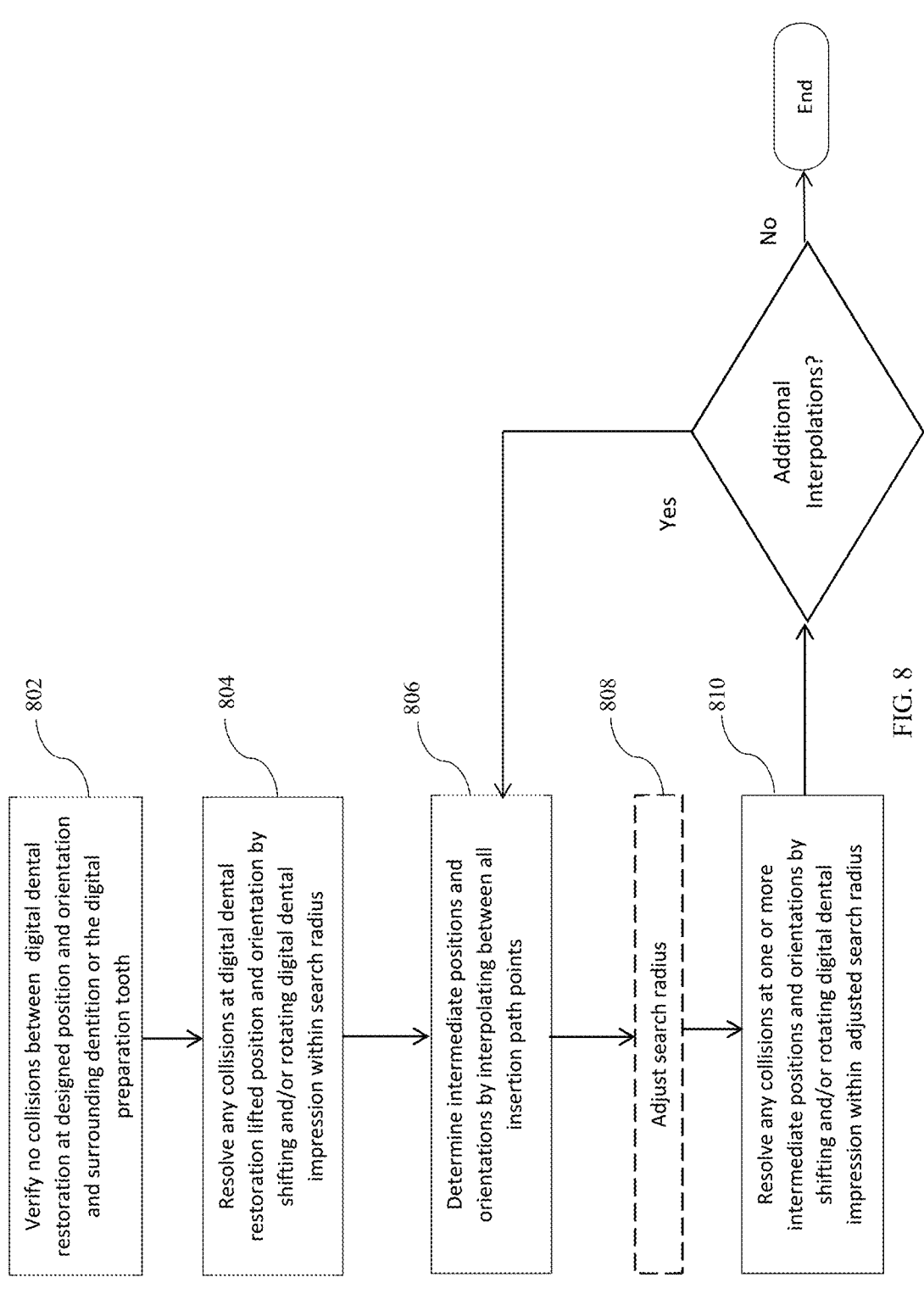
FIG. 8 is a flow chart illustrating an example of determining an insertion path in some embodiments.

FIG. 8 illustrates an example of a computer-implemented method with one or more features in some embodiments. The computer-implemented method can verify no collisions between digital dental restoration at designed position and orientation and surrounding dentition or the digital preparation tooth at 802, resolve any collisions at digital dental restoration lifted position and orientation by shifting and/or rotating digital dental impression within search radius at 804, determine intermediate positions and orientations by interpolating between all insertion path points at 806, optionally adjust the search radius at 808, resolve any collisions at one or more intermediate positions and orientations by shifting and/or rotating digital dental impression within the adjusted search radius at 810, and repeat steps 806, 808, and 810 until no more interpolations are left.

Figure 9:
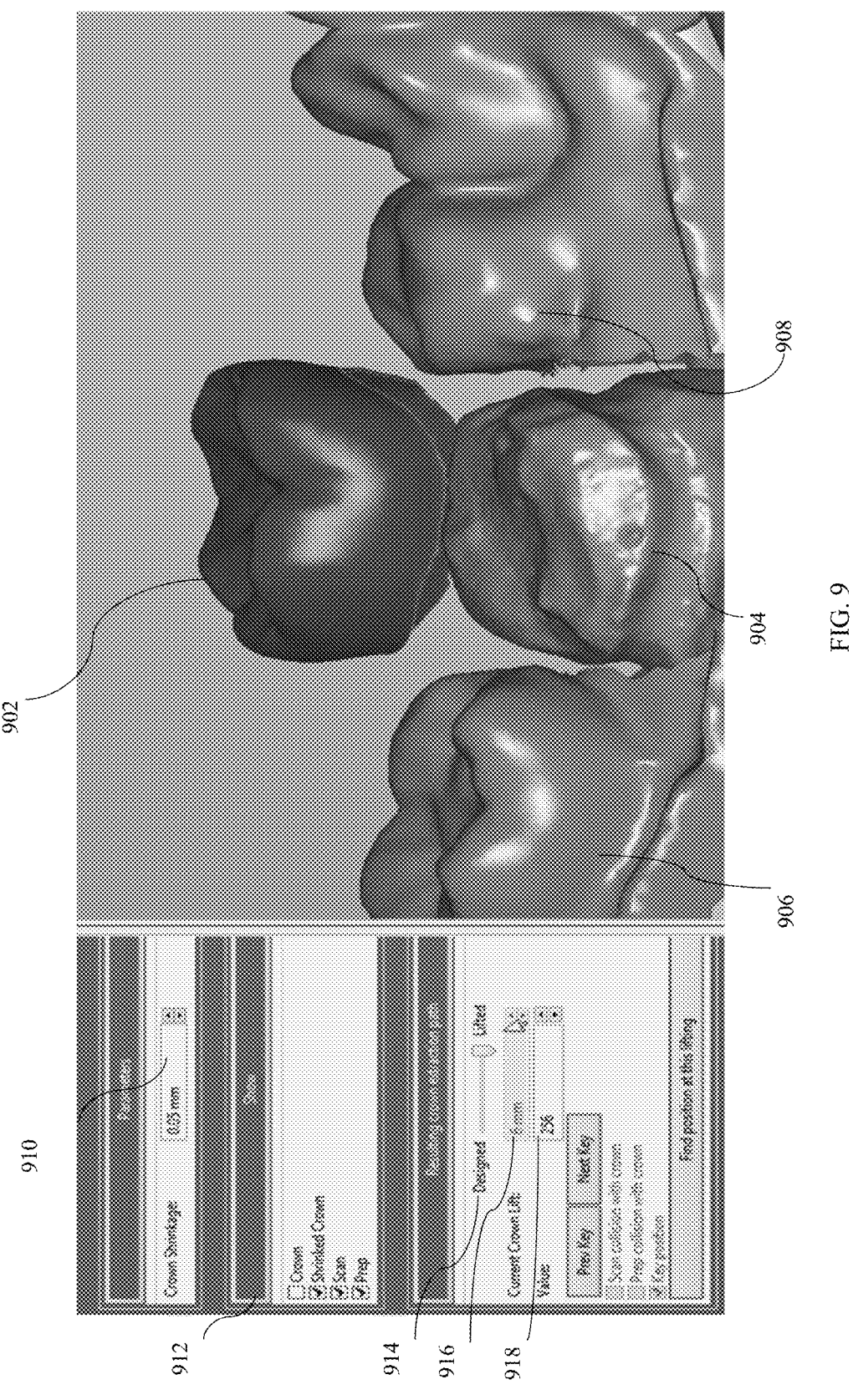
FIG. 9 is an example of a Graphical User Interface in some embodiments.

FIG. 9 illustrates a GUI in some embodiments that can be output on a display device and which the user can interact with through one or more input devices, for example and view on the display device. The figure shows a reduced digital dental restoration 902, a digital restoration tooth 904 and surrounding dentition that includes first neighboring tooth 906 and second neighboring tooth 908. In some embodiments, a user can set the digital dental restoration reduction size via the input field 910, for example. In some embodiments, the user can also choose what to display based on selection boxes in the show section 912. For example, the user can elect to show the digital dental restoration (such as, for example, a crown), the reduced digital dental restoration (such as a shrunken crown, for example), the scan data which can include the surrounding dentition ("Scan"), and the digital preparation tooth ("Prep"). The GUI can provide an input field such as a slider 914 to show the reduced digital dental restoration 902 move along the insertion path from a designed position and orientation to a lifted position and orientation, for example. The GUI can also provide an input field 916 in which the user can specify the lift position distance. For example, in the figure, the lift position distance is set to 6 mm. The GUI can also provide an interpolation segment number input field 918 which determines how many segments are part of the insertion path. This can determine the number of interpolation steps the computer-implemented method performs since for example $2^x$=(number of segments in the interpolation), where x is the number of interpolation steps performed. For example, in the figure, the interpolation segment number input field 918 is set to 256, so that the number of interpolation steps would be 8 ($2^8$=256).

Some embodiments include a non-transitory computer readable medium storing executable computer program instructions for digital dental restoration insertion, the computer program instructions including instructions for: digitally determining a virtual insertion path of a digital dental restoration to a digital preparation tooth, the virtual insertion path including a plurality of insertion path positions and corresponding insertion path orientations.

The computer program instructions can include one or more optional features in any combination. For example, the collision-free virtual insertion path can be within a tolerance. The tolerance can be one or more selected from the group consisting of a manufacturing tolerance and a scanning tolerance. One or more regions of the digital dental restoration can be reduced in size based on the tolerance. The tolerance can be a user-configurable value. The method can an also include flagging the digital dental restoration when virtual insertion path is not within the tolerance. An initial virtual insertion path position of the virtual insertion path can start from a lifted position and can terminate on the digital preparation tooth. Determining the virtual insertion path can include interpolating one or more intermediate digital dental restoration positions and corresponding digital dental restoration orientations from the lifted position to the digital preparation tooth. The one or more intermediate digital dental restoration positions and corresponding intermediate digital dental restoration orientations can be free of collisions with surrounding dentition. The lifted position and the corresponding lifted orientation can be free of collisions with surrounding dentition. Determining the virtual insertion path can be performed automatically by the computer-implemented method. The digital dental restoration can be one or more selected from the group consisting of a digital crown, a bridge, an inlay, and an outlay. The virtual insertion path can be collision-free. The virtual insertion path can be collision-free with surrounding digital dentition. The virtual path can be collision-free with the digital restoration tooth.

One or more advantages of one or more features can include, for example, determination of the insertion path. Using shifting and rotating can advantageously, for example, potentially provide, for example numerous, granular movements, and can provide many options to avoid collisions. One advantage can include, for example, in cases where collisions cannot be avoided, the computer-implemented method can still determine an insertion path and provide feedback of unavoidable collisions, for example. One advantage can include, for example, the ability to determine a insertion path position and orientation while also determining its collision-free position and orientation by shifting and/or rotating, for example. One advantage can include determining an insertion path and resolving any collisions before manufacturing the physical digital dental restoration. One advantage can include, for example, avoiding the cost, material, and time to develop a physical model. One advantage can include, for example, being less time-consuming, less expensive, and more precise compared to using physical models, for example.

Some embodiments include a processing system for digital dental restoration insertion verification, including, for example: a processor, a computer-readable storage medium including instructions executable by the processor to perform steps including: digitally determining a virtual insertion path of the digital dental restoration to the digital preparation tooth, the virtual insertion path comprising a plurality of insertion path positions and corresponding insertion path orientations.

The computer program instructions can include one or more optional features in any combination. For example, the collision-free virtual insertion path can be within a tolerance.

The tolerance can be one or more selected from the group consisting of a manufacturing tolerance and a scanning tolerance. One or more regions of the digital dental restoration can be reduced in size based on the tolerance. The tolerance can be a user-configurable value. The method can an also include flagging the digital dental restoration when virtual insertion path is not within the tolerance. An initial virtual insertion path position of the virtual insertion path can start from a lifted position and can terminate on the digital preparation tooth. Determining the virtual insertion path can include interpolating one or more intermediate digital dental restoration positions and corresponding digital dental restoration orientations from the lifted position to the digital preparation tooth. The one or more intermediate digital dental restoration positions and corresponding intermediate digital dental restoration orientations can be free of collisions with surrounding dentition. The lifted position and the corresponding lifted orientation can be free of collisions with surrounding dentition. Determining the virtual insertion path can be performed automatically by the computer-implemented method. The digital dental restoration can be one or more selected from the group consisting of a digital crown, a bridge, an inlay, and an outlay. The virtual insertion path can be collision-free. The virtual insertion path can be collision-free with surrounding digital dentition. The virtual path can be collision-free with the digital restoration tooth.

Figure 10:
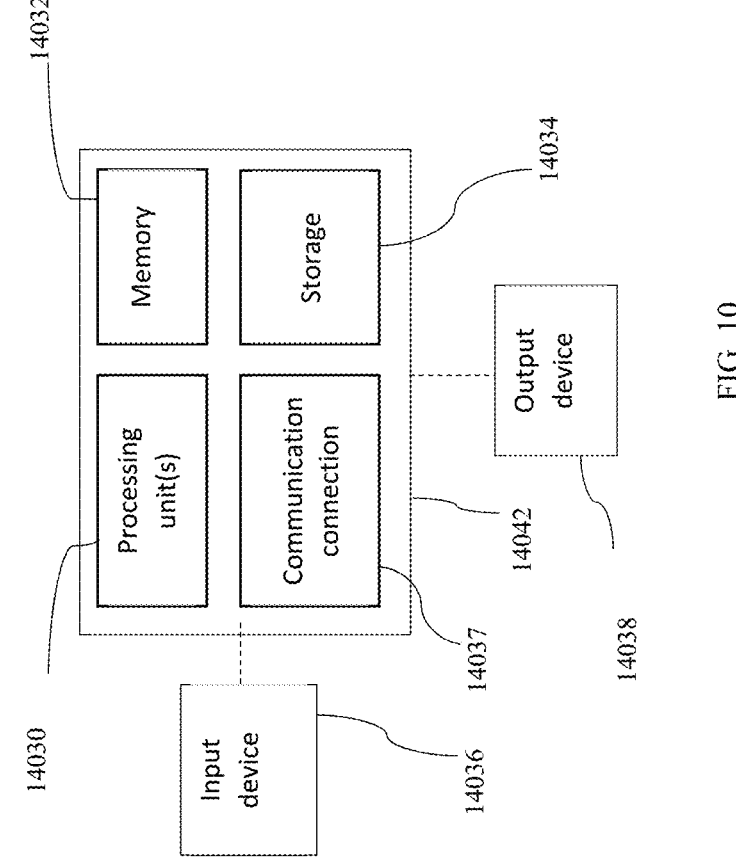
FIG. 10 is a diagram illustrating a system in some embodiments.

FIG. 10 illustrates a processing system 14000 in some embodiments. The system 14000 can include a processor 14030, computer-readable storage medium 14034 having instructions executable by the processor to perform one or more steps described in the present disclosure. In some embodiments, for example, the instructions can include steps to perform: digitally determining a virtual insertion path of the digital dental restoration to the digital preparation tooth, the virtual insertion path including a plurality of path positions and corresponding digital dental restoration orientations. The instructions can include several optional features as discussed, and can include other features disclosed. In some embodiments, digital dental restoration insertion verification can be initiated by a user using an input device while viewing the digital model on a display, for example. In some embodiments, the computer-implemented method can allow the input device to manipulate the digital model displayed on the display. For example, in some embodiments, the computer-implemented method can rotate, zoom, move, and/or otherwise manipulate the digital model in any way as is known in the art. In some embodiments the computer-implemented method can display the digital model on a display and receive input from an input device such as a mouse or touch screen on the display for example. The computer-implemented method can, upon receiving an initiation command, perform digital dental restoration insertion verification using one or more features described in the present disclosure. The computer-implemented method can, upon receiving manipulation commands, rotate, zoom, move, and/or otherwise manipulate the digital model in any way as is known in the art.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication mediums. Such suitable communication mediums include, for example, the Internet, the World Wide Web, an intranet, software applications, cable (including fiber optic cable), magnetic communications, electromagnetic communications (including RF, microwave, and infrared communications), electronic communications, or other such communication mediums.

In view of the many possible embodiments to which the principles of the disclosure may be applied, it should be recognized that the illustrated embodiments are only examples and should not be taken as limiting the scope of the disclosure.

What is claimed is:

1. A computer-implemented method of digital dental restoration insertion verification, comprising:

receiving a digital model comprising a digital dental restoration and a digital preparation tooth;

adjusting the digital dental restoration to provide a reduced digital dental restoration to account for tolerances;

determining an initial virtual insertion path position and orientation of the reduced digital dental restoration as a lifted position from the digital preparation tooth at which no collisions occur;

digitally determining one or more intermediate positions toward the digital preparation tooth;

digitally determining a collision free position and orientation at the one or more intermediate positions, and providing the digital dental restoration to computer aided manufacturing ("CAM") and generating a physical dental restoration based on the digital dental restoration, wherein digitally determining the collision free position and orientation is performed in parallel at one or more position and orientation combinations, wherein digitally determining the collision free position and orientation comprises evaluating only those shift positions in which a maximum displacement of reduced digital dental restoration surface points to a particular shift position is within a user-configurable search radius.

2. The method of claim 1, wherein determining the collision free position and orientation comprises performing one or more from the group consisting of shifting and rotating the reduced digital dental restoration upon determining a collision.

3. The method of claim 2, wherein the reduced digital dental restoration shifting is performed along the x-y axis.

4. The method of claim 2, wherein the collision is between the reduced digital dental restoration and one or more neighboring teeth.

5. The method of claim 1, wherein the one or more intermediate positions are determined by interpolation.

6. The method of claim 1, wherein the one or more intermediate positions are within a user-configurable bounding volume.

7. The method of claim 1, further comprising selecting the first determined collision-free position and orientation as an intermediate virtual insertion path position and orientation.

8. A non-transitory computer readable medium storing executable computer program instructions to provide digital dental restoration insertion verification, the computer program instructions comprising instructions for:

receiving a digital model comprising a digital dental restoration and a digital preparation tooth;

adjusting the digital dental restoration to provide a reduced digital dental restoration to account for tolerances;

determining an initial virtual insertion path position and orientation of the reduced digital dental restoration as a lifted position from the digital preparation tooth at which no collisions occur;

digitally determining one or more intermediate positions toward the digital preparation tooth;

digitally determining a collision free position and orientation at the one or more intermediate positions, and providing the digital dental restoration to computer aided manufacturing ("CAM") and generating a physical dental restoration based on the digital dental restoration, wherein digitally determining the collision free position and orientation is performed in parallel at one or more position and orientation combinations, wherein digitally determining the collision free position and orientation comprises evaluating only those shift positions in which a maximum displacement of reduced digital dental restoration surface points to a particular shift position is within a user-configurable search radius.

9. The medium of claim 8, wherein determining the collision free position and orientation comprises performing one or more from the group consisting of shifting and rotating the reduced digital dental restoration upon determining a collision.

10. The medium of claim 9, wherein the collision is between the reduced digital dental restoration and one or more neighboring teeth.

11. The medium of claim 8, wherein the one or more intermediate positions are determined by interpolation.

12. The medium of claim 8, wherein the one or more intermediate positions are within a user-configurable bounding volume.

13. The medium of claim 8, further comprising selecting the first determined collision-free position and orientation as an intermediate virtual insertion path position and orientation.

14. A system for digital dental restoration insertion verification, the system comprising:

a processor; and a non-transitory computer-readable storage medium comprising instructions executable by the processor to perform steps comprising:

receiving a digital model comprising a digital dental restoration and a digital preparation tooth;

adjusting the digital dental restoration to provide a reduced digital dental restoration to account for tolerances;

determining an initial virtual insertion path position and orientation of the reduced digital dental restoration as a lifted position from the digital preparation tooth at which no collisions occur;

digitally determining one or more intermediate positions toward the digital preparation tooth;

digitally determining a collision free position and orientation at the one or more intermediate positions, and providing the digital dental restoration to computer aided manufacturing ("CAM") and generating a physical dental restoration based on the digital dental restoration, wherein digitally determining the collision free position and orientation is performed in parallel at one or more position and orientation combinations, wherein digitally determining the collision free position and orientation comprises evaluating only those shift positions in which a maximum displacement of reduced digital dental restoration surface points to a particular shift position is within a user-configurable search radius.

15. The system of claim 14, wherein determining the collision free position and orientation comprises performing one or more from the group consisting of shifting and rotating the reduced digital dental restoration upon determining a collision.

16. The system of claim 15, wherein the collision is between the reduced digital dental restoration and one or more neighboring teeth.

17. The system of claim 14, wherein the one or more intermediate positions are determined by interpolation.

18. The system of claim 14, wherein the one or more intermediate positions are within a user-configurable bounding volume.

19. The system of claim 14, further comprising selecting the first determined collision-free position and orientation as an intermediate virtual insertion path position and orientation.

* * * * *